US006489119B1

(12) United States Patent
Miller et al.

(10) Patent No.: US 6,489,119 B1
(45) Date of Patent: Dec. 3, 2002

(54) ANALGESIC SCREENING METHOD AND COMPOSITION

(75) Inventors: James L. Miller, Los Altos, CA (US); George P. Miljanich, Redwood City, CA (US); Stephen S. Bowersox, Menlo Park, CA (US); Laszlo Nadasdi, Walnut Creek, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/454,714

(22) Filed: Dec. 6, 1999

Related U.S. Application Data (63) Continuation of application No. 08/829,452, filed on Mar. 28, 1997, now abandoned.
(60) Provisional application No. 60/014,437, filed on Mar. 29, 1996.

(51) Int. Cl.[7] .......................... C12Q 1/00; G01N 33/53; G01N 33/566; A61K 49/00; A61K 31/535
(52) U.S. Cl. ............................. 435/7.1; 435/4; 435/7.2; 435/7.21; 435/967; 436/8; 436/63; 436/149; 436/501; 436/806; 436/815; 424/9.1; 424/9.2; 514/237.8; 514/238.8; 514/255; 514/315; 514/567; 514/626; 514/428; 514/613; 564/194

(58) Field of Search ................ 424/9.1, 9.2; 514/237.8, 514/238.8, 255, 315, 567, 626, 428, 613; 435/4, 7.1, 7.2, 7.21, 967; 436/8, 63, 149, 501, 806, 815; 564/194

(56) References Cited

U.S. PATENT DOCUMENTS

| 3,988,473 | A | * | 10/1976 | Adams et al. | 424/324 |
|---|---|---|---|---|---|
| 4,022,899 | A | * | 5/1977 | Adams et al. | 424/251 |
| 5,319,105 | A | * | 6/1994 | Kolaczwowski et al. | 549/223 |
| 5,364,842 | A | * | 11/1994 | Justice et al. | 514/12 |
| 5,424,218 | A | * | 6/1995 | Miljanich et al. | 436/503 |
| 5,559,095 | A | * | 9/1996 | Miljanich et al. | 514/12 |
| 5,670,622 | A | * | 9/1997 | Shon et al. | 530/324 |
| 6,054,429 | A | * | 4/2000 | Bowersox et al. | 514/12 |
| 6,087,091 | A | * | 6/2000 | Justice et al. | 435/4 |
| 6,156,726 | A | * | 12/2000 | Newcomb et al. | 514/12 |
| 6,166,085 | A | * | 12/2000 | Chaplan et al. | 514/626 |
| 6,174,690 | B1 | * | 1/2001 | Manger et al. | 435/7.21 |

* cited by examiner

Primary Examiner—Long V. Le
Assistant Examiner—Kartic Padmanabhan
(74) Attorney, Agent, or Firm—Leslie J. Boley

(57) ABSTRACT

Disclosed is a method of selecting analgesic agents based on their selective ability to block tetrodotoxin-insensitive sodium channels, particularly in comparison to blocking tetrodotoxin-sensitive sodium channels. Also disclosed is a novel class of compounds that is selective for blocking tetrodotoxin-insensitive sodium channels.

7 Claims, 8 Drawing Sheets

ANALGESIC SCREENING METHOD AND COMPOSITION

This application is a continuation of U.S. Pat. application having Ser. No. 08/829,452, filed Mar. 28, 1997, abandoned which claims priority to Provisional U.S. Pat. application having Ser. No. 60/014,437, filed Mar. 29, 1996, both of which are herein incorporated by reference.

FIELD OF THE INVENTION

The present invention relates to a screening method for identifying analgesic compositions and to a novel class of analgesic agents.

REFERENCES

Akopian, A. N., et al., *Nature* 379:257–262 (1996).
Arbuckle, J. B. and R. J. Docherty, *Neurosci. Lett.* 185:70–73 (1995).
Del-Bianco, E., et al., *Neurosci. Lett.* 170:163–166 (1994).
Elliott, A. A. and J. R. Elliott, *J. Physiol.* 463:39–56 (1993).
Fernando, C. R. et al., *J. Med. Chem.* 23:1153–1158 (1980).
Glushkov, R. G. et al., U.S. Pat. No. 1,557,964 (7/92); Derwent Abstract No. 93-224958.
Gold, M. S., et al., *Proc. Natl. Acad. Sci.* (USA) 93:1108–1112 (1996).
Hamill O. P., et al., *Pflugers Arch.* 391:85–100 (1981).
Jeftinija, S., *Brain Research* 639:125–134 (1994).
Keenaghan, J. B. et al., *J. Pharmacol. Exp. Ther.* 180:454 (1972).
Lawson, S. N., et al., *Brain Res. Bull.* 30:239–243 (1993).
Marsh, S. J., et al., *Neuroscience* 23:275–289 (1987).
Martin, H. A., et al., *Neuroscience* 22:651–659 (1987).
Nelson, S. D. et al., *J. Pharrm. Sci.* 66:1180–1190 (1977).
Oh, U., et al., *J. Neurosci.* 16:1659–1667 (1996).
Roy, M. L. and T. Narahashi, *J. Neurosci.* 12:2104–2111 (1992).
Treede, R. D., et al., *Prog. Neurobiol.* 38:397–421 (1992).
Treede, R. D., *Annals of Medicine* 27:213–216 (1995).

BACKGROUND OF THE INVENTION

Chronic or intractable pain, such as may occur in conditions such as bone degenerative diseases and cancer, is a debilitating condition which is treated with a variety of analgesic agents, and often opioid compounds, such as morphine.

While brain pathways governing the perception of pain are still incompletely understood, sensory afferent synaptic connections to the spinal cord, termed "nociceptive pathways" have been documented in some detail. In the first leg of such pathways, C- and A-fibers are primary afferents which project from peripheral sites to the spinal cord, carrying nociceptive signals. Polysynaptic junctions in the dorsal horn of the spinal cord are involved in the relay and modulation of sensations of pain to various regions of the brain, including the periaqueductal grey region. Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminals and which, when they fire, inhibit release of neurotransmitters, including substance P. Descending pathways from the brain are also inhibitory on C- and A-fiber firing.

Mammalian dorsal root ganglia (DRG) contain several subtypes of primary afferent neurons. Afferent neurons in dorsal root ganglia receive input from axons that originate in the periphery and terminate in the dorsal horn of the spinal cord. These signals are carried by action potentials and are coded by the rate that action potentials invade synaptic termini in the dorsal horn. DRG neurons transmit information concerning muscle length and tension, touch, joint movement, temperature, as well as, fast and slow pain. DRG neurons that subserve the perception of pain are termed nociceptors or primary afferent nociceptors (PANs; Treede, 1995). PANs are distinguishable from other DRG neuron-subtypes by their small diameter axons (both myelinated and unmyelinated), a small diameter cell body (Lawson, et al., 1993) and by the presence of capsaicin-sensitive receptors that are coupled to non-selective cation channels (Marsh, et al., 1987; Martin, et al., 1987; Oh, et al., 1996). PANs become sensitized by sustained noxious stimuli and inflammatory mediators. Sensitization is manifested by a reduction in threshold and by a response increase (i.e. the firing rate of action potentials; Treede, 1992). The sensitization of PANs is thought to underlie hyperalgesia and may also contribute to some neuropathic pain states (Treede, 1995).

Blocking the signals carried by PANs leads to analgesia. Analgesia may be achieved by preventing the initiation of the signal, by blocking signal transmission along the PANs between the sensory ending and pre-synaptic terminal, or by blocking synaptic signal transmission in the dorsal horn of the spinal cord. For example, the local anesthetics are believed to block pain signals by blocking voltage-gated sodium (Na) channels in PANs and thus preventing the signal from reaching the presynaptic terminal.

DRG neurons that carry different types of sensory information transmit their signals using a number of voltage- and ligand-dependent ion channels. Of particular interest in the context of analgesia are the Na channel subtypes expressed in DRG and other neuron types. Na channels in PANs are dominated by a subtype that is insensitive to the neurotoxin tetrodotoxin (tetrodotoxin-insensitive (TTXi) Na channel; Akopian, et al., 1996; Arbuckle, et al., 1995; Gold, et al., 1996; Jeftinija, 1994). However, most neurons, such as motor neurons, also express significant levels of TTX-sensitive Na channels (TTXs Na channel; Elliot; Roy).

It would be desirable to selectively block Na channels enriched in PANs while avoiding the inhibition of Na channels expressed in other neuron subtypes, to reduce adverse side effects, while still effecting analgesia. For example, while lidocaine and other local anesthetics can act as potent analgesics, because they block TTXs Na channels, they can produce serious side effects, including spinal block, respiratory blockade and cardiac arrest. These compounds must be administered with great caution.

It is the discovery of the present invention that agents that preferentially block TTXi Na channels over TTXs Na channels are particularly useful as analgesic agents and represent a significant improvement over existing local anesthetics. We describe herein, a new class of agents, exemplified by SNX-483 (3-hydroxy monoethylglycinexylidide, 3-OH MEG-X), that selectively block TTXi Na channels in mammalian PANs, as well as a screening assay for identifying these and similar compounds.

SUMMARY OF THE INVENTION

In one aspect, the invention includes a method of selecting compounds for use in producing analgesia. The general method includes measuring the ability of test compounds to block tetrodotoxin-insensitive (TTXi) sodium channels. A compound is selected as an analgesic agent if it is at least 1/10 as potent as 3-hydroxy monoethylglycinexylidide (3-OH-MEGX) in locking such channels. In another embodiment, the compound will be equipotent to 3-OH-MEGX in this locking activity.

The method includes further measuring the ability of the test compound to block tetrodotoxin-sensitive (TTXs) sodium channels. Desirable compounds selected by this embodiment of the method will be selected if they exhibit potency ratios of at least 2 in blocking TTXI sodium channels as compared to blocking TTXs sodium channels. In a preferred embodiment, the potency ratio for comparing blockade of TTXi and TTXs is calculated according to the formula:

Potency ratio=$1(IC_{50, TTXi}/IC_{50, TTXs})$, where $IC_{50, TTXi}$ is the concentration of compound effective to inhibit current through the TTXi sodium channel by 50%, and $IC_{50, TTXs}$ is the concentration of compound effective to inhibit current through the TTXs sodium channel by 50%.

In another embodiment, the compound selection includes monitoring the compound for its ability to reversibly block said TTXi sodium channel in a cell bathing solution in an electrophysiological assay of TTXI sodium channels. A compound is selected if not more than 5–15% of a sodium current that passes through the TTXi sodium channel recovers after said compound is removed from the cell bathing solution. Such recovery is preferably measured over a time frame of 5–30 minutes of continuous perfusion of the cell preparation following removal of compound from the cell bathing solution.

In alternate embodiments, blockade of TTX-insensitive channels can be measured either by electrophysiological means, such as in the electrophysiological assays described herein, or by ligand binding displacement assays, also described herein. In such a ligand displacement, a preferred ligand is 3-hydroxy monoethylglycinexylidide (3-OH-MEGX).

In a related aspect, the invention includes a composition comprising a 3-hydroxy monoethylglycinexylidide analog that is effective to block TTXi sodium channels with a potency that is at least about one-tenth as great as the potency exhibited by 3-hydroxy monoethylglycinexylidide in blocking such TTXi sodium channels. More preferably, the composition will exhibit a potency that is at least as great as the potency exhibited by 3-hydroxy monoethylglycinexylidide in blocking TTX-insensitive channels. The compound is also characterized by a potency ratio in blocking TTXi sodium channels, as compared to blocking TTXs sodium channels, of at least 2, as described above.

These and other objects and features of the invention will become more fully apparent when the following detailed description of the invention is read in conjunction with the accompanying drawings.

BRIEF DESCRIPTION OF THE DRAWINGS

FIGS. 2 (A–D) shows sodium conductances of a DRG neuron exposed to depolarizing voltage steps from a holding potential of –80 mV to voltages between –40 mV and +20 mV in the absence of compound (A), in a pulsed-pair paradigm (B), expansion of the rapidly recovering TTXi current observed in panel B (C), and the TTXs current generated by subtraction (D);

DETAILED DESCRIPTION OF THE INVENTION

Definitions

The term "potency", as used herein refers to the ability of a compound to elicit a particular biological activity. A compound's potency is usually expressed as the molar concentration of the compound to achieve a particular level of activity. Two compounds are "equipotent" if they achieve the same effect at about the same respective molar concentrations. One measure of potency is the concentration of a compound that is effective to block a current by 50%, e.g., the $IC_{50}$ of the compound.

The term "potency ratio" refers to the ratio of potencies of a compound measured in different assays.

Using $IC_{50}$ as an exemplary measure of potency, a potency ratio for inhibition of sodium currents in TTXi and TTXs assays is calculated as follows:

Potency ratio (TTXi/TTXs)=$1/(IC_{50, TTXi}/IC_{50, TTXs})$.

The term "tetrodotoxin-insensitive sodium channel" or "TTX-insensitive Na channel" or "TTXi Na channel" refers to a sodium channel with an $IC_{50}$ for TTX of greater than 60–100 $\mu$M.

The term "tetrodotoxin-sensitive Na channel" or "tetrodotoxin-sensitive Na channel" or "TTXs Na channel" refers to a sodium channel that is sensitive to blockade by TTX at concentrations of 10 $\mu$M or less. Both TTXi and TTXi sodium channels are better defined by their descriptions herein.

The terms "block", "inhibit" and declinations thereof, as used in the context of channel blockade, refer to diminution of or complete cessation of ion flow through the channel when the channel is in an open state, as evidenced by decreased current measurement.

I. Analgesic 3-Hydroxy Monoethylglycinexylidide Derivatives or Analogs

In the context of the present invention, analgesic analogs or derivatives of 3-hydroxy monoethylglycinexylidide (3-OH-MEGX; 3-hydroxy MEGX) are those which are effective in blocking tetrodotoxin-insensitive (TTXi) Na channels. By "blocking" is meant that at a membrane potential between –70 mV and –45 mV these compounds block TTXi Na channels with a potency that is at one-tenth ($\frac{1}{10}$) the potency exhibited by 3-hydroxy monoethylglycinexylidide.

More specifically, in the same range of membrane potentials, the selectivity of the analogs in blocking TTXi sodium channels is measured relative to their abilities to block TTX-sensitive (TTXs) Na channels. Analgesic 3-hydroxy MEGX analogs within the meaning of the present invention are those that have a potency ratio of TTXi/TTXs of two (2) or greater, where the potency ratio is calculated according to the formula:

$$\text{Potency Ratio of (TTXi/TTXs)}=1/(IC_{50,\ TTXi}/IC_{50,\ TTXs}).$$

Here, the analog's ability to block the TTXs sodium channels is measured relative to the ability of the parent compound 3-OH-MEGX to block such channels. Preferably, the analgesic analog will have no greater effect on conductance through such TTXs sodium channels as does 3-OH-MEGX.

According to a further feature of the invention, analgesic analogs also exhibit poor reversibility ("washout") in an electrophysiological assay. That is, when cells containing TTXi or TTXs sodium channels are exposed to compound in a flow-through cell recording chamber, and then the cells are further washed with compound-free medium, the blockade of the sodium current exhibited by the compound is not substantially diminished. For example, at a membrane potential of –55 mV, only 5–15% of the sodium current recovers after SNX-483 is removed from the solution bathing the cell. (See, for example FIG. 4).

Therefore, in accordance with the invention, and as discussed below, analgesic 3-OH-MEGX analogs are identified and selected by first producing a chemical derivative or congener of 3-OH-MEGX, then testing it for ability to block TTXi sodium channels, using one or more of the methods described herein, and further testing it for its effect on TTXs sodium channels. Compounds which have profiles similar to that exhibited by 3-OH-MEGX will be considered analgesic analogs in the present context. The analgesic properties of such compounds can then be verified in any of a number of standard experimental animal models of analgesia, such as the rat tail-flick test, the rat formalin model, or models of peripheral neuropathy, such as the Chung model. Such assays are well known in the art and are described, for example in U.S. Pat. No. 5,587,454, incorporated herein by reference.

A. Preparation of 3-Hydroxy Monoethylglycine-xylidide Analogs

Figure 1A:
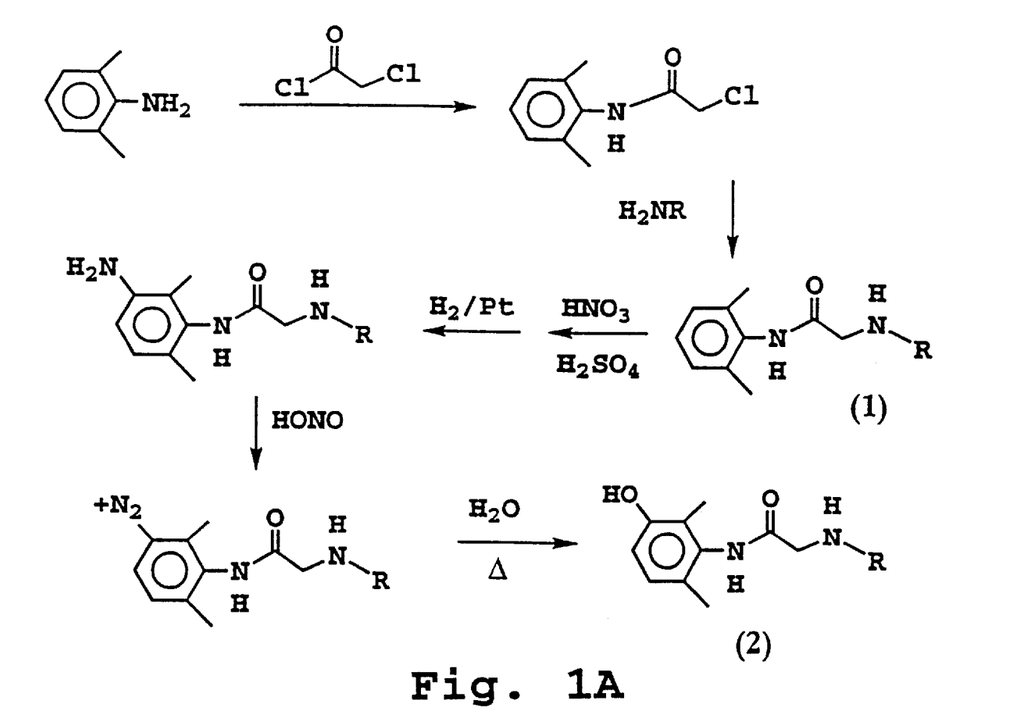
FIG. 1 shows a synthetic scheme for the preparation of 3-OH-MEGX.

A reaction scheme for the parent compound, 3-OH-MEGX is shown in FIG. 1A and detailed in Example 1. The compound is also referred to as "SNX-483" herein. This reaction scheme can be modified to produce analogs of interest, according to methods known in the art.

Analogs having a 3-hydroxy substituent on the benzene ring may generally be prepared according to methods described in, e.g., Keenaghan, Nelson, and Glushkov, all of which are incorporated herein by reference, as shown in FIG. 1A. As in standard syntheses of lidocaine, 2,6-xylidine is first acylated with chloroacetyl chloride, or, alternatively, with the reaction product of chloroacetic acid with acetic anhydride (Glushkov), to give 2-chloro-N-(2,6-dimethylphenyl) acetamide. Reaction with an appropriately substituted amine gives a 2-alkylamino-N-(2,6-dimethylphenyl) acetamide (1). Nitration of the benzene ring, followed by diazotization and hydrolysis (Keenaghan) gives the phenol, a 2-alkylamino-N-(3-hydroxy2,6-dimethylphenyl) acetamide (2).

Figure 1B:
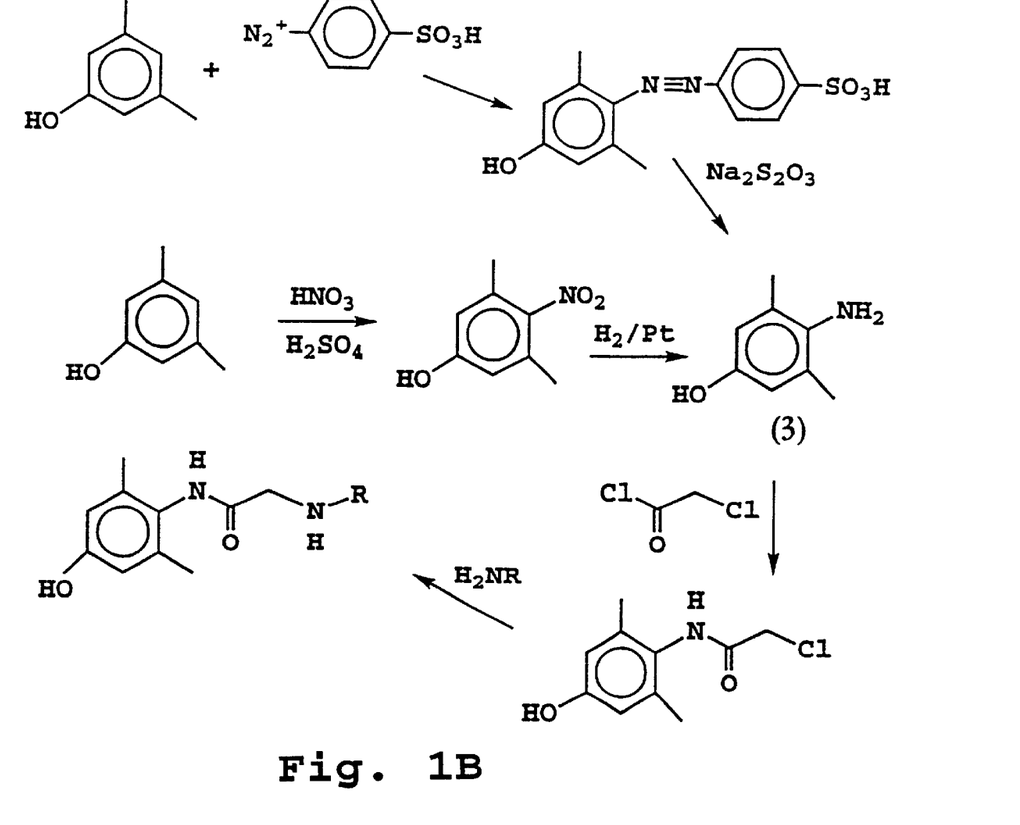

Compounds having 4-hydroxy substitution may be prepared as shown generally in FIG. 1B. The intermediate, 4-hydroxy-2,6-xylidine, or 4-amino-3,5-dimethylphenol (3), can be prepared by known methods. Of the two possible routes shown, one employs nitration of 3,5-dimethylphenol, isolation of the 4-nitro isomer, and reduction to the amine. The alternate route, which follows a method described in Fernando, incorporated herein by reference, uses an azo intermediate formed by coupling of 3,5-dimethylphenol with diazotized sulfanilic acid. The azo compound is then reduced to the amine, in a reported overall yield of 89%. Subsequent acylation and alkylation give the substituted acetamide, as described for FIG. 1A.

Compounds having additional reactive groups, such as polar substituents, may be prepared by employing suitable protecting groups during synthesis.

Further analogs may be prepared by variations on the schemes of FIGS. 1A and 1B, according to well known synthetic methods. For example, compounds having a two-carbon linkage between the carbonyl group and amine nitrogen are prepared by substituting 3-chloropropionyl chloride for chloroacetyl chloride.

Figure 1C:
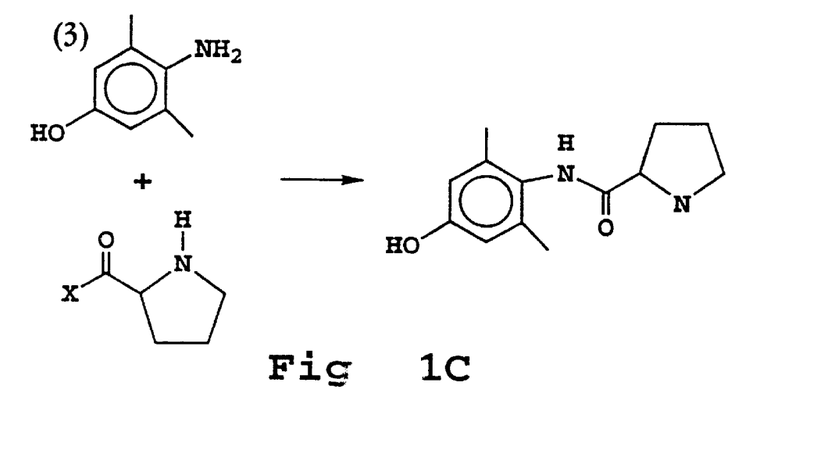

Compounds having a heterocyclic ring in the side chain may be prepared by reaction of an appropriate carboxyl-substituted nitrogen heterocycle, such as an activated proline, with 4-amino-3,5-dimethylphenol, shown in FIG. 1C, or 3-amino-2,4-dimethyl phenol, which may be prepared from 2,6-xylidine using reactions shown in FIG. 1A.

Exemplary 3-OH-MEGX compounds suitable for testing in the screening assay described herein include analogs described in co-owned U.S. Patent Application entitled "Method and Compositions for Producing Analgesia" (U.S.S.N. 08/818,489 filed Mar. 14, 1997, which is hereby incorporated herein by reference.

B. Analgesic Analogs of 3-OH-MEGX

As discussed above, in accordance with the present invention, analgesic analogs of 3-OH-MEGX are those compounds that not only share the basic structure of 3-OH-MEGX, as discussed above, but which also share its biochemical specificity in blocking TTXi Na channels. Analogs of 3-OH-MEGX will generally include variations in the position and nature of substituents, particularly alkyl and hydroxyl substituents, within the compound. For example, hydroxyl substitution may be at the 3- or 4-position of the benzene ring. The side chain amine nitrogen, which is preferably a secondary amine, may be substituted with various alkyl groups, such as methyl, ethyl, isopropyl, and the like. Groups having 1 to 4 carbons are preferred. These alkyl groups may be further substituted, preferably with polar groups. The amine nitrogen may also be contained within a heterocyclic ring, such as a pyrrolidine, as shown in FIG. 1C.

Analgesic analogs are further identified using the screening methods described in Section II, below. That is, the practitioner will, in accordance with standard principles of chemical substitution, make a modification to the 3-OH MEGX structure shown as (2) in FIG. 1A, and then will test the compound in one or more of the various Na channel blockade or binding assays described below. Analgesic analogs will exhibit a selectivity for blockade of TTXi Na channels that is similar to that exhibited by 3-OH-MEGX. Optimally, such analgesic analogs are as potent as 3-OH-MEGX in blocking TTXi, measured, for example, using an electrophysiological assay or using a displacement binding assay, as discussed below. In this context, the term "equipotent" is generally meant to signify that an equivalent molar amount of compound is effective in producing approximately the same degree of blockade of the channel. In practical terms, this may mean that the compound has a similar $IC_{50}$ for blocking the channel or has a similar affinity ($K_i$) for the channel.

Moreover, in accordance with the present invention, analogs of 3-OH-MEGX are preferred to have very little, or significantly reduced effect on TTX-sensitive Na channels, as compared to their effects on TTXi Na channels. This attribute is desirable to reduce unwanted side effects, such as respiratory blockade, that occur when TTXs sodium channels are blocked.

II. Methods of Selecting Analgesic Compounds

A. Selective Blockade of TTX-insensitive Sodium Channels

Blockade of TTX insensitive sodium channels is conveniently measured in an electrophysiological assay as detailed in Example 2 or in a binding displacement assay as described below. Results of experiments carried out in support of the present invention are discussed below.

As illustrated in FIG. 2, nociceptive neurons contain both TTXi and TTXs Na currents. FIG. 2A presents whole-cell currents of a capsaicin-sensitive DRG neuron in response to voltage steps from a holding potential of −80 mV to test potentials between −40 and +60 mV. Under these conditions, the observed current is the sum of TTXs and TTXi Na currents (Elliot, Gold). These currents are identified as originating from Na-selective conductances by a reduction in current amplitude when NaCl is isoosmotically replaced with dextrose and by a reversal potential near +40 mV consistent with that predicted by the Nernst Equation.

TTXi Na currents were usually isolated by addition of 10 $\mu$m TTX or by exploiting the rapid recovery of TTXi Na currents following a 100 ms prepulse to −10 mV, as in FIG. 2 (Elliot). Using a voltage paradigm during which a pair of depolarizing steps to −10 mV are separated by a 4 ms repolarizing step, greater than 90% of TTXs Na currents remain inactivated (FIG. 2B, see below). FIGS. 2C and 2D present voltage families of the TTXi (rapidly recovering Na current) and TTXs (slowly recovering Na current), respectively, generated using this paired-pulse paradigm. TTXs currents (FIG. 2D) were generated by subtracting Na currents obtained following a prepulse to −10 mV from those obtained without a prepulse. The fraction of the total Na current carried by the fast-recovering, TTXi, Na channel varied from cell to cell (generally from 70–90% of Na current is carried by a TTXi conductance in capsaicin-sensitive DRGs). Regardless of the relative contribution of TTXs and TTXi Na currents to the total Na current, the paired-pulse paradigm reproducible and reliably isolated a >90% TTXi current as confirmed by subsequent application of a 10 $\mu$M TTX solution.

Figure 3:
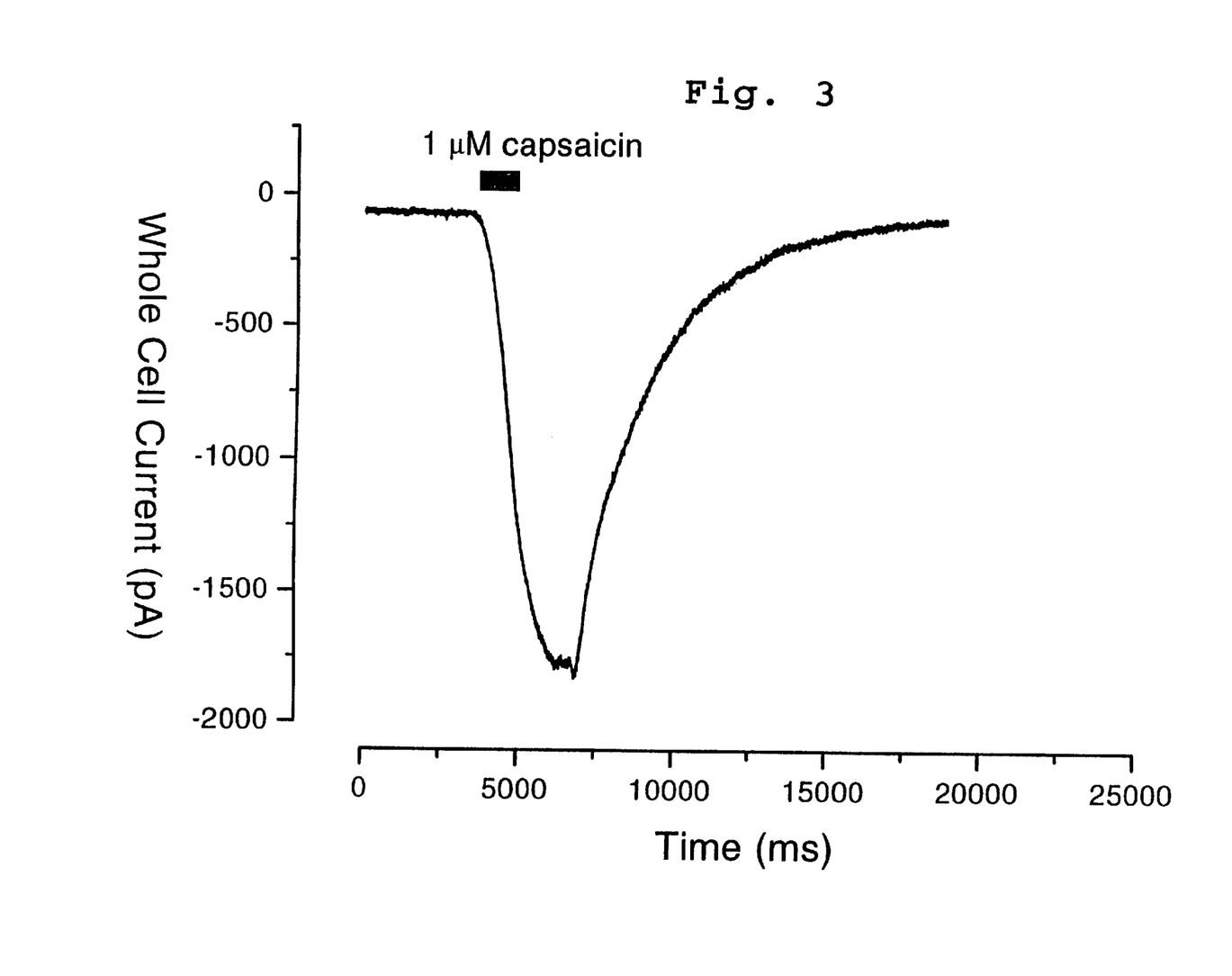
FIG. 3 shows capsaicin sensitivity (0.5 s exposure to 1 $\mu$M capsaicin) of a primary afferent nociceptor.

Nociceptive DRG neurons were identified by their small diameter cell bodies. Their identities were confirmed by a large inward current generated in response to a brief 0.5–1 s exposure to a solution containing 0.5 or 1 $\mu$M capsaicin. FIG. 3 shows a typical response to a 0.5 s exposure to 1 $\mu$M capsaicin.

1. Effect of 3-OH MEGX on TTXi Sodium Channels.

Figure 4:
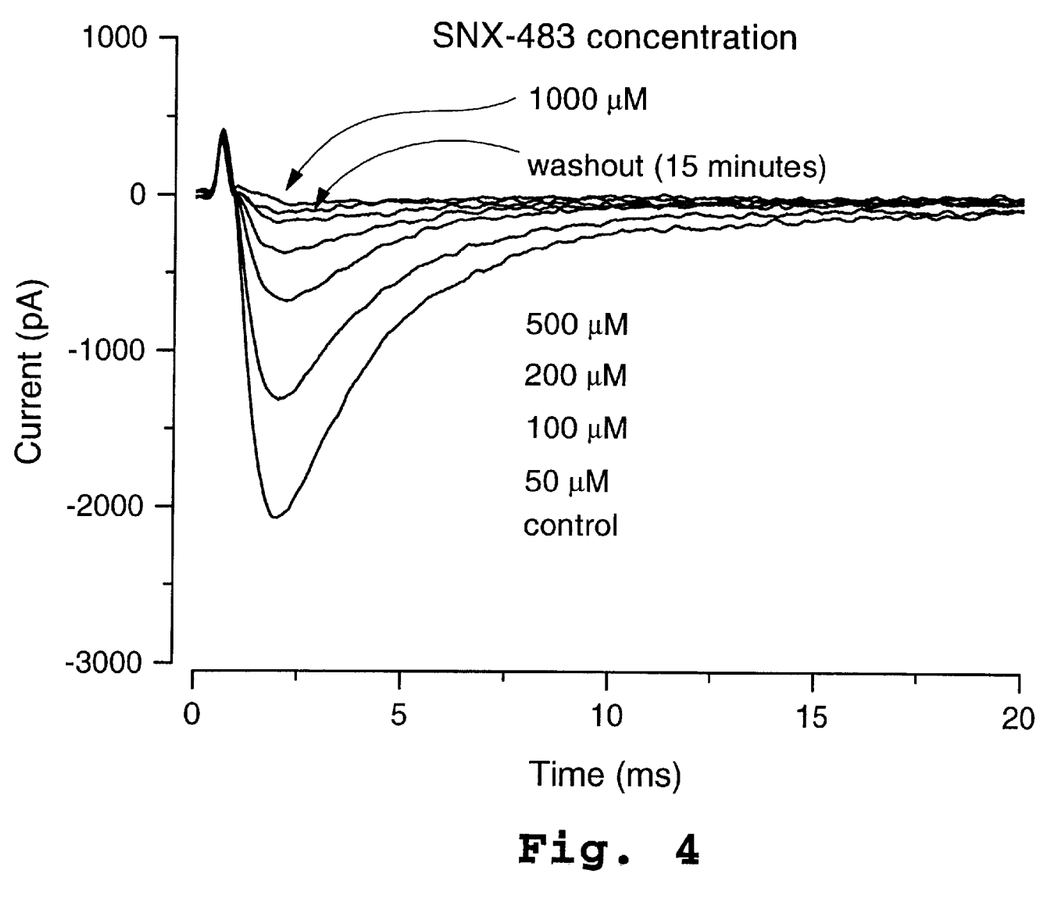
FIG. 4 shows TTXI sodium currents obtained in the presence of 10 $\mu$M TTX (control) and in the presence of 10 $\mu$M TTX with 50, 100, 200, 500 and 1000 $\mu$M SNX-483 (sequentially added) in a capsaicin-sensitive DRG, and following continuous superfusion with the control solution in the absence of SNX-483 ("washout")

FIG. 4 presents Na currents obtained before and after exposure of cells to solutions containing 50, 100, 200, 500 and 1000 $\mu$M SNX-483 in a capsaicin-sensitive DRG neuron (PAN). SNX-483 was found to block TTXi Na currents with an $IC_{50}$ of approximately 70 $\mu$M. In the experiments presented in FIG. 4, the capsaicin-sensitive neuron was held at −55 mV and stepped twice to −10 mV at 10 second intervals. Similar results have been obtained in every capsaicin-sensitive PAN tested (n=7). Only about 7% of the TTXi Na current that was blocked by 400 $\mu$M SNX-483 recovered within 15 minutes of continuously exchanging the recording chamber with fresh extracellular solution. This lack of "washout" is an additional characteristic of analgesic compounds of the present invention.

Figure 5:
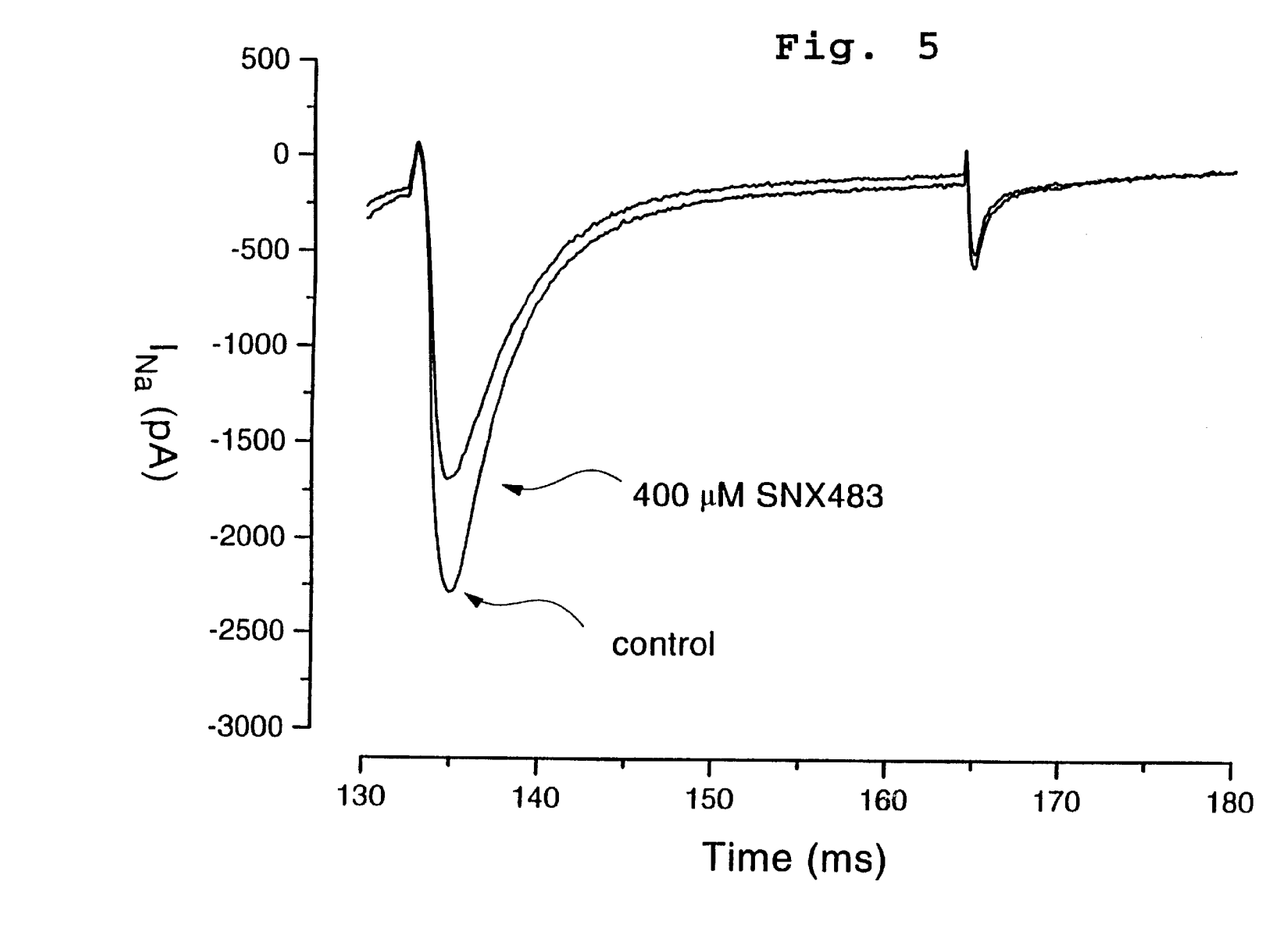
FIG. 5 shows reduction of TTXi Na currents at hyperpolarized holding potentials.

FIG. 5 demonstrates that the potency of SNX-483 is significantly reduced when the holding membrane potential is increased to −80 mV. Following depolarizing steps in membrane potential from −80 mV, 400 $\mu$M SNX-483 blocks only 20% of the TTXi Na current.

Similar results have been obtained in every capsaicin-sensitive DRGs tested (n=5).

2. Effect of 3-OH MEGX on TTXs Sodium Currents.

Figure 7:
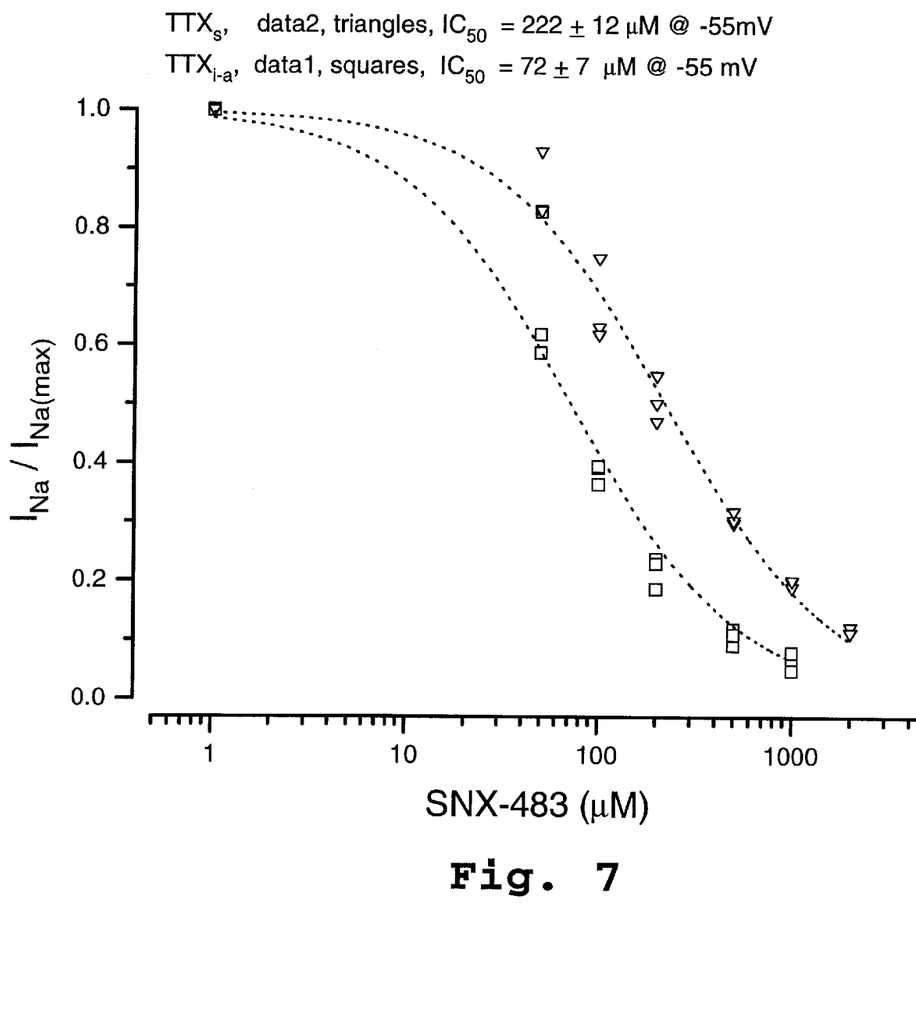
FIG. 7 shows a plot of normalized TTXi and TTXs sodium currents (membrane potential –55 mV) as a function of SNX-483 concentration.

FIG. 7 illustrates that at a membrane potential of −55 mV, SNX-483 more potently blocks TTXi Na currents than TTXs Na currents. In experiments carried out in support of the present invention, DRGs containing predominantly TTXi Na currents and TTXs currents were superfused sequentially with increasing concentrations of SNX-483. Data for inhibition of TTXi currents were obtained by adding 10 $\mu$M TTX to the superfusion medium to block TTXs currents present in the preparation.

The $IC_{50}$ of SNX-483 for TTXi currents was 72±7 $\mu$M; the $IC_{50}$ of SNX-483 for TTXs currents was 222±12 $\mu$M. A potency ratio calculated according to the formula $1(IC_{50, TTXi}/IC_{50, TTXs})$ is 3.1.

3. Selectivity of 3-OH-MEGX for TTXi Sodium Channels over Calcium and Potassium Channels.

In parallel experiments, SNX-483 was tested for its ability to block voltage-dependent calcium (Ca) and voltage-dependent potassium (K) channels. N- and L-type Ca channel-mediated Ca fluxes were measured fluorometrically using INDO1—loaded IMR32 and GH3 cells, respectively. At concentrations exceeding 300 AM (the highest concentration tested), SNX-483 had no effect on either type of Ca flux.

In addition, SNX-483 was evaluated for the ability to inhibit members of the Shaker subfamily of voltage-dependent K channels expressed in xenopus oocytes. At concentrations up to 1 $\mu$M, SNX-483 had no effect on K currents mediated by Kv1.1, Kv1.2, Kv1.3 or Kv1.4 K channels.

Analgesic 3-OH-MEGX analogs selected in accordance with the present invention should exhibit a similar pharmacological profile to that described for 3-OH-MEGX herein. That is, when tested in a TTXi Na channel assay, they should block passage of sodium current through the channel with a potency that is at least about 1/10 the potency of 3-OH-MEGX, and they should exhibit a potency ratio of at least 2 in a comparison of blockade of TTXi and TTXs sodium channels, as described herein.

B. Competitive Displacement Assay

In accordance with the present invention, selectivity of test compounds for TTXi Na channel blockade can also be assessed in a competitive binding assay set up to measure displacement of 3-OH-MEGX or an analog or congener thereof from membranes or cells containing TTXi sodium channels. Such preparations, and methods for setting up such assays are well known to those familiar with the art.

Briefly, membranes are prepared from a TTXi sodium channel containing preparation, such as DRG. Test compounds are added to the preparation and assessed for their abilities to displace binding of labeled ligand, such as radiolabeled 3-OH-MEGX. The relative potency of displacement is determined according to standard procedures, by determining an $IC_{50}$ and/or $K_i$ for each test compound. Test compounds having potencies in displacing such binding that are within the range of potency measured for 3-OH-MEGX (i.e., at having an $IC_{50}$ that is less than or 10–100-fold higher (preferably not more than about 10-fold higher) than the $IC_{50}$ measured for 3-OH-MEGX are selected as analgesic agents using this assay. It should be noted that further testing in an electrophysiological assay, such as described in Part A, above, may be necessary, to validate antagonist (as opposed to agonist) activity at the channel; however, such verification is within the ability of the practitioner in the art.

Further, to assess selectivity, the compound may be tested in a TTXs binding assay, such as by measuring ability to displace TTX from a preparation containing TTXs sodium channels. Potency ratios can be calculated using the formula presented above, or preferably, substituting $K_i$ values for $IC_{50}$ values to yield the equation: $1/(K_{i,\ TTXi}/K_{i,\ TTXs})$ The following examples illustrate, but in no way are intended to limit the present invention. All references referred to herein are incorporated by reference in their entireties.

EXAMPLE 1

Synthesis of 3-OH-MEGX Analogs

As illustrated in FIG 1A., 2,6-xylidine is first acylated with chloroacetyl chloride, or, alternatively, with the reaction product of chloroacetic acid with acetic anhydride, in accordance with standard synthetic procedures used to produce lidocaine (Glushkov, et al., 1992), to give 2-chloro-N-(2,6-dimethylphenyl) acetamide (Akopian, et al., 1996). Reaction with ethylamine gives 2-(ethylamino)-N-(2,6-dimethylphenyl) acetamide (Arbuckle and Docherty, 1995). Nitration of the benzene ring, followed by diazotization and hydrolysis (Keenaghan, et al., 1972) gives the phenol, 2-(ethylamino)-N-(3-hydroxy-2,6-dimethylphenyl) acetamide, or 3-hydroxy MEGX (Del-Bianco, et al., 1994).

It is recognized that derivatives or analogs of 3-OH-MEGX can be prepared using analogous reactions to those described above, or by carrying out standard chemical reactions on 3-OH-MEGX, to achieve the desired substitution. Examples of reaction schemes are presented in FIG. 1B and FIG. 1C. For those reactions or assays in which a labeled product is to be used, the compound can be radiolabeled, as by tritiation, or otherwise tagged, such as by fluorophores, according to methods well known in the art.

EXAMPLE 2

Electrophysiological Assays for Blockade of Sodium Channels

A. Primary Culture of DRG Neurons

10–20 day old Sprague-Dawley rat pups were euthanized using $CO_2$ or decapitation. Dorsal root ganglia were removed and placed in Dulbecco s Minimum Essential Medium supplemented with 10% (v/v) fetal bovine serum (DMEM). Ganglia were then cut into small pieces and transferred to DMEM containing 2 mg/ml collagenase and incubated for 30 minutes in a 37° C. incubator with 5% $CO_2$ atmosphere. After 15 minutes incubation, the pieces were gently triturated by three passages through a glass capillary pulled to 0.2 mm i.d. The collagenase was then removed by three washes in 10 ml of DMEM. The final resuspension was into DMEM supplemented with 50 ng/ml NGF, 50 I.U./ml penicillin and 50 mg/ml streptomycin. Cells were then transferred onto glass coverslips coated with collagen and placed in a 37° C. incubator as above.

C. Solutions used for Electrical Measurements on Cells

The extracellular solution contained (in mM): NaCl, 50; Tetraethylammonium chloride, 30; Choline chloride, 80; $CaCl_2$, 0.1; $MgCl_2$, 5; HEPES, 10; dextrose, 5; pH 7.35, p=317 mOsm. The intracellular solution contained (in mM): CsCl, 140; NaCl, 3; $CaCl_2$, 0.1; EGTA, 11; $MgCl_2$, 4; MOPS, 10; $Na_2ATP$, 2; $Na_3GTP$, 1; pH 7.27, p=311 mOsm (Gold, et al., 1996). Lidocaine, SNX-483 and capsaicin were dissolved in extracellular solution.

D. Electrical Measurements

Currents were obtained using tight seal electrodes in the whole-cell recording configuration (Hamill, et al., 1981). Membrane voltage control and whole-cell current records were obtained using an Axopatch 200A amplifier (Axon Instruments, Foster City, Calif.) controlled by computer (PCLAMP6, Axon Instruments, Foster City Calif.). Signals were lowpass filtered below 5 kHz. Electrodes were fabricated using thick-walled borosilicate glass and pulled to achieve a resistance of 0.5–3 MΩ. Lidocaine- and SNX-483-containing solutions were introduced via bath perfusion.

Capsaicin-containing solutions were used to identify PANs and were introduced through a superfusion pipet (i.d. 30 μm) positioned approximately 100–150 mm from the cell. The recording chamber was continuously perfused with extracellular solution (1–2 ml/min) during capsaicin application.

E. Measurement of Sodium Currents

1. Measurement of Total Sodium Currents

Figure 2A:
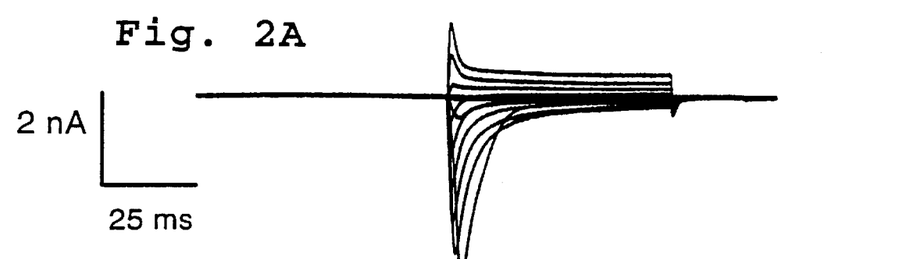

Total Na currents of a DRG neuron were elicited by depolarizing voltage steps from a holding potential of –80 mV to voltages between –40 mV and +20 mV in 10 mV increments (FIG. 2A). A paired-pulse paradigm (Elliott and Elliott, 1993) was used to isolate the rapidly-recovering, TTXi, Na current. During the first depolarizing voltage step, the membrane potential was stepped from a holding potential of –80 mV to –10 mV for 60 ms. Following a 4 ms repolarizing step to –80 mV, the membrane potential is stepped to voltages between –40 mV and +60 mV in 10 mV increments. Results of such a treatment are shown in FIG. 2B, while FIG. 2C shows expansion of the rapidly-recovering, TTXi, Na current obtained by the paradigm presented in Panel B.

2. Measurement of TTX-sensitive currents

Figure 2B:
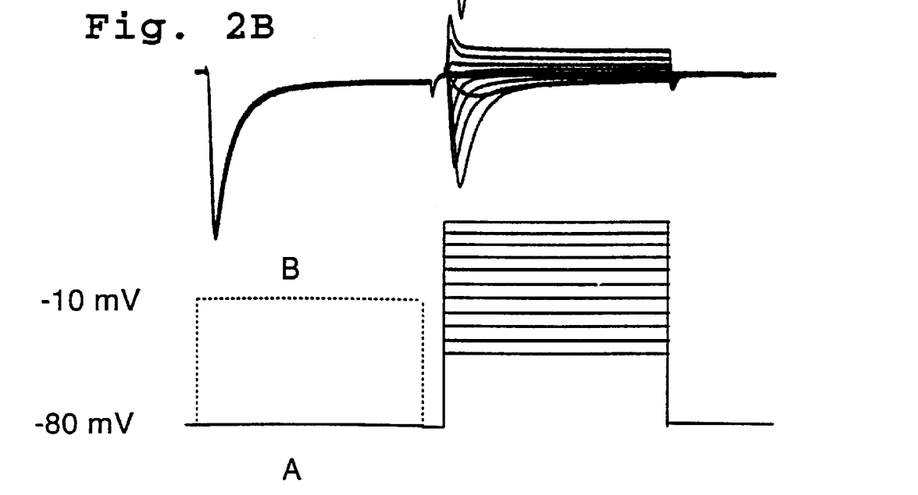
Figure 2C:
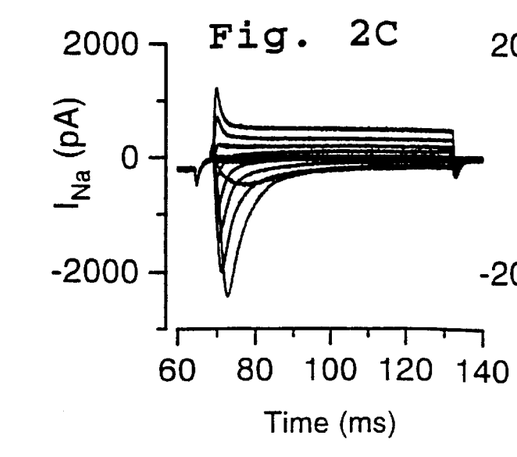
Figure 2D:
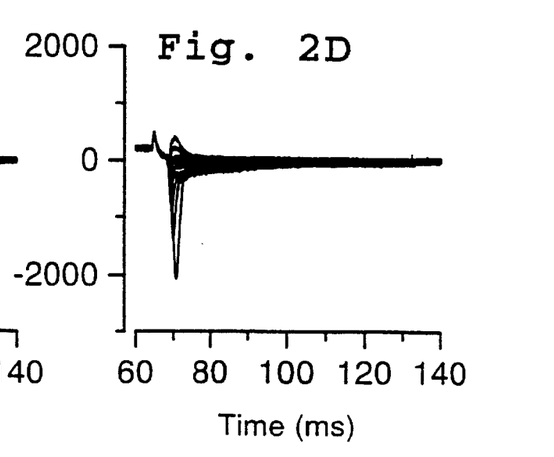

A TTXs Na current was generated by subtracting the rapidly-recovering, TTXi, Na currents shown in FIG. 2B from the total Na current shown in FIG. 2A. The individual sweeps were initiated at 10 s intervals. In all panels presented here, Na currents have been corrected for leak using the P/4 procedure. At the holding potential of –80 mV, a standing inward current of approximately –120 pA was observed, and this remained constant throughout the recording.

Alternatively, TTXs currents can be measured in neurons or cultured neurons known in the art to lack TTXi sodium channels, such as may be found in large DRGs, cell lines, and the superior cervical ganglion.

F. Identification of Primary Afferent Nociceptor by Activation of Capsaicin-Dependent Currents After obtaining a whole-cell recording of a small diameter DRG the membrane potential was voltage-clamped at –80 mV. While continuously exchanging the recording chamber with fresh extracellular solution, a brief exposure to a 1 μM solution of capsaicin was applied using a superfusion pipet positioned 150 mm from the cell (indicated by the bar above the current trace in FIG. 3). This elicited a large inward current that slowly recovered as the solution in the recording chamber was exchanged. The record shown in FIG. 3 is not leak corrected for a steady leak of approximately –70 pA. Na currents obtained before and after application of 1 μM capsaicin were identical.

G. Effects of SNX-483 (3-OH MEGX) on Sodium Currents in Capsaicin-Sensitive DRG (Nociceptive Neurons)

Na currents were recorded in the absence (labeled control) and presence of 50, 100, 200, 400 and 1000 μM SNX-483 in a capsaicin-sensitive DRG, as shown in FIG. 4. The capsaicin-sensitive neuron was held at −55 mV and stepped twice to −10 mV at 10 second intervals. The membrane potential was voltage-clamped at −55 mV between individual sweeps and during the 4 ms repolarizing voltage step between the conditioning prepulse to −10 mV and the second voltage step to −10 mV. Individual sweeps were repeated at 10 second intervals. The currents elicited by the first depolarizing pulse are shown.

H. Effects of Compound on Neurons at Hyperpolarized Holding Potentials

Generally, as illustrated in FIG. 5, blockade of TTXi Na currents is reduced at hyperpolarized holding potentials. Na currents in a capsaicin-sensitive DRG, voltage-clamped at −80 mV between paired depolarizing voltage steps to −10 mV and separated by a 4 ms repolarizing voltage step to −80 mV are shown. For clarity, the currents elicited by the 100 ms prepulse are not shown in the figure. The current traces were recorded in extracellular solution in the absence (CTRL) and presence of 400 μM SNX-483.

I. Measurement of Tetrodotoxin-Sensitive Sodium Currents

Figure 6:
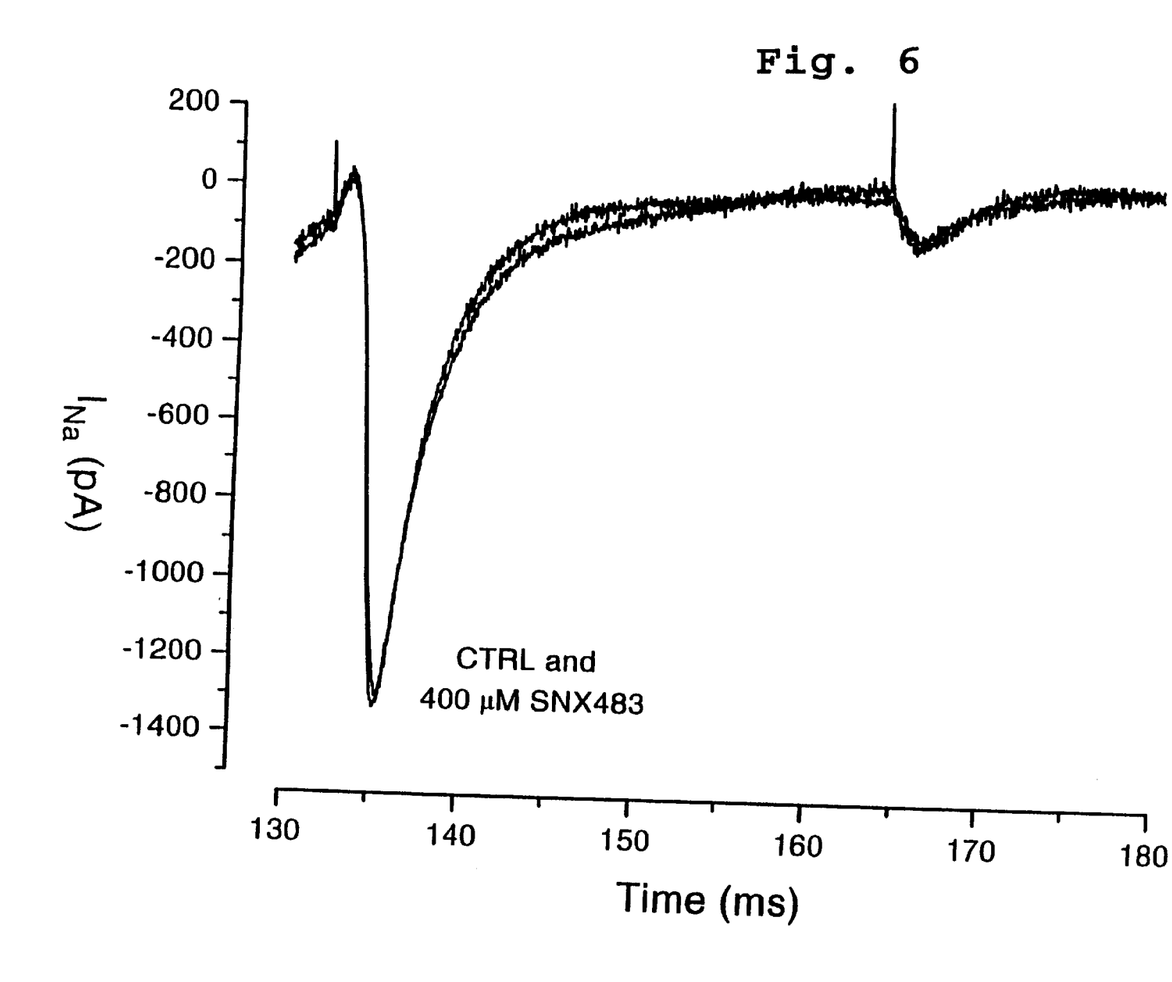
FIG. 6 shows effect of 400 $\mu$M SNX-483 (3-OH-MEGX) on TTXs sodium currents where duration of repolarizing voltage step was increased to 16 msec to allow TTXs sodium channels time to recover.

TTXs sodium currents can be measured in large DRG neurons or in other cells or cell lines lacking TTXi Na channels. FIG. 6 shows the electrophysiological profile of a large, capsaicin-insensitive, DRG that was voltage-clamped at −55 mV between paired depolarizing voltage steps to −10 mV. The duration of the repolarizing voltage step to −55 mV between steps to −10 mV was increased to 16 ms to permit most of the TTXs current to recover. For clarity, the currents elicited by the 100 ms prepulse are not shown in the figure. 400 μM SNX-483 does not block TTXs Na currents.

FIG. 7 illustrates results of experiments carried in which DRGs containing predominantly TTXi Na currents and TTXs currents were superfused sequentially with increasing concentrations of SNX-483. Data for inhibition of TTXi currents were obtained by adding 10 μM TTX to the superfusion medium to block any TTXs currents present in the preparation. The $IC_{50}$ of SNX483 for TTXi currents was 72±7 AM; the $IC_{50}$ of SNX-483 for TTXs currents was 222±12 AM. A potency ratio calculated according to the formula $1/(IC_{50, TTXi}/IC_{50, TTXs})$ is 3.1.

While the invention has been described with reference to specific methods and embodiments, it will be appreciated that various modifications and changes may be made without departing from the invention.

What is claimed is:

1. A method of selecting a compound for use in producing analgesia in a subject, comprising measuring an ability of said compound to block tetrodotoxin-insensitive (TTXi) sodium channels and to block tetrodotoxin-sensitive (TTXs) sodium channels, and selecting the compound if (i) it exhibits a potency in blocking TTXi sodium channels that is at least about one-tenth as great as the potency exhibited by 3-hydroxy monoethylglycinexylidide in blocking said TTXi sodium channels, and (ii) it exhibits a potency ratio of at least 2 in blocking said TTXi sodium channels as compared to blocking said TTXs sodium channels, wherein the selected compound produces analgesia in the subject.

2. The method of claim 1, wherein said compound is selected if its potency in inhibiting said TTXi sodium channels is at least as great as that of 3-hydroxy monoethylglycinexylidide in blocking said channels.

3. The method of claim 1, wherein said potency ratio of blocking said TTXi and said TTXs sodium channels is measured by a formula: $1(IC_{50, TTXi}/IC_{50, TTXs})$, where $IC_{50, TTXi}$ is a concentration of compound effective to inhibit current through said tetrodotoxin-insensitive sodium channel by 50%, and $IC_{50, TTXs}$ is a concentration of said compound effective to inhibit current through said tetrodotoxin-sensitive sodium channel by 50%.

4. The method of claim 1, wherein said compound is further monitored for its ability to reversibly block said TTXi sodium channels in a cell bathing solution in an electrophysiological assay of tetrodotoxin-insensitive sodium channels and is selected if, at −55 mV, following removal of said compound from the cell bathing solution, less than 5–15% of the blockade of the sodium current exhibited by the compound is diminished.

5. The method of claim 1, wherein said measuring of tetrodotoxin-insensitive sodium channel blockade is by electrophysiological means.

6. The method of claim 1, wherein said measuring of tetrodotoxin-insensitive sodium channel blockade is carried out in a ligand displacement assay.

7. The method of claim 6, wherein a ligand used in the ligand displacement assay is 3-hydroxymonoethylglycinexylidide.

* * * * *